United States Patent
Kerboul et al.

(10) Patent No.: US 9,220,542 B2
(45) Date of Patent: Dec. 29, 2015

(54) SYSTEM AND METHOD FOR A LOCKABLE POLYAXIAL DRIVER TOOL

(71) Applicants: Guillaume Kerboul, Quimper (FR); James William Truscott, Swindon (GB); Stuart G. Weekes, Oxford (GB)

(72) Inventors: Guillaume Kerboul, Quimper (FR); James William Truscott, Swindon (GB); Stuart G. Weekes, Oxford (GB)

(73) Assignee: TECOMET, INC, Warsaw, IN (US)

( * ) Notice: Subject to any disclaimer, the term of this patent is extended or adjusted under 35 U.S.C. 154(b) by 179 days.

(21) Appl. No.: 13/713,137

(22) Filed: Dec. 13, 2012

(65) Prior Publication Data

US 2013/0150906 A1      Jun. 13, 2013

Related U.S. Application Data

(60) Provisional application No. 61/570,082, filed on Dec. 13, 2011.

(51) Int. Cl.
| | | |
|---|---|---|
| *A61B 17/70* | (2006.01) | |
| *A61B 17/80* | (2006.01) | |
| *A61F 2/46* | (2006.01) | |
| A61F 2/30 | (2006.01) | |
| A61F 2/44 | (2006.01) | |

(52) U.S. Cl.
CPC ............ *A61B 17/7074* (2013.01); *A61B 17/808* (2013.01); *A61F 2/4611* (2013.01); *A61F 2002/30538* (2013.01); *A61F 2002/30774* (2013.01); *A61F 2002/30777* (2013.01); *A61F 2002/30787* (2013.01); *A61F 2002/4475* (2013.01); *A61F 2002/4629* (2013.01)

(58) Field of Classification Search
CPC ...................... A61F 2/44–2/447; A61F 2/4611
USPC ........... 606/86 A, 86 R, 99; 623/17.11–17.16
See application file for complete search history.

(56) References Cited

U.S. PATENT DOCUMENTS

| | | | |
|---|---|---|---|
| 1,470,421 A * | 10/1923 | Astley | 81/447 |
| 3,732,621 A * | 5/1973 | Bostrom | 433/174 |
| 6,287,115 B1 * | 9/2001 | Lustig et al. | 433/173 |
| 7,892,239 B2 | 2/2011 | Warnick et al. | |
| 7,959,675 B2 | 6/2011 | Gately | |
| 7,976,549 B2 | 7/2011 | Dye et al. | |
| 7,988,695 B2 | 8/2011 | Dye | |
| 8,043,293 B2 * | 10/2011 | Warnick | 606/86 A |
| 8,241,362 B2 * | 8/2012 | Voorhies | 623/17.16 |
| 8,241,364 B2 * | 8/2012 | Hansell et al. | 623/17.16 |
| 8,252,060 B2 * | 8/2012 | Hansell et al. | 623/17.16 |

(Continued)

*Primary Examiner* — Eduardo C Robert
*Assistant Examiner* — Michelle C Eckman
(74) *Attorney, Agent, or Firm* — AKC Patents LLC; Aliki K. Collins

(57) ABSTRACT

A polyaxial driver system for inserting and setting the angular orientation of an implant includes an elongated component and a distal component. The elongated component extends along a main axis and includes an elongated tubular sheath and an elongated shaft disposed within the tubular sheath. The distal component is pivotally connected to a distal end of the elongated shaft and includes a tubular body extending along the main axis and a spherical head dimensioned to fit and move freely within the tubular body. A proximal end of the elongated shaft includes a first set of outer threads and a proximal end of the elongated tubular sheath includes inner threads shaped and dimensioned to engage the first set of outer threads of the elongated shaft. Rotating the elongated tubular sheath clockwise or counter-clockwise moves the elongated shaft forward or backward along the main axis, respectively.

17 Claims, 4 Drawing Sheets

(56) References Cited

U.S. PATENT DOCUMENTS

| | | | |
|---|---|---|---|
| 2001/0021853 A1 | 9/2001 | Heckele et al. | |
| 2006/0111728 A1* | 5/2006 | Abdou | 606/86 |
| 2006/0253120 A1* | 11/2006 | Anderson et al. | 606/86 |
| 2007/0093850 A1* | 4/2007 | Harris et al. | 606/99 |
| 2007/0093897 A1* | 4/2007 | Gerbec et al. | 623/17.11 |
| 2007/0142843 A1* | 6/2007 | Dye | 606/99 |
| 2007/0213737 A1* | 9/2007 | Schermerhorn et al. | 606/86 |
| 2008/0009880 A1 | 1/2008 | Warnick et al. | |
| 2008/0027544 A1* | 1/2008 | Melkent | 623/17.11 |
| 2008/0065082 A1* | 3/2008 | Chang et al. | 606/85 |
| 2008/0077150 A1* | 3/2008 | Nguyen | 606/85 |
| 2008/0077241 A1* | 3/2008 | Nguyen | 623/17.11 |
| 2008/0091211 A1* | 4/2008 | Gately | 606/99 |
| 2008/0140085 A1* | 6/2008 | Gately et al. | 606/99 |
| 2008/0167660 A1* | 7/2008 | Moreau et al. | 606/104 |
| 2008/0221694 A1* | 9/2008 | Warnick et al. | 623/17.16 |
| 2008/0243133 A1* | 10/2008 | Heinz | 606/104 |
| 2008/0269904 A1* | 10/2008 | Voorhies | 623/17.16 |
| 2008/0306489 A1* | 12/2008 | Altarac et al. | 606/99 |
| 2009/0030423 A1* | 1/2009 | Puno | 606/99 |
| 2009/0036877 A1* | 2/2009 | Nardone et al. | 606/1 |
| 2009/0222092 A1* | 9/2009 | Davis et al. | 623/17.11 |
| 2009/0276049 A1* | 11/2009 | Weiland | 623/17.16 |
| 2010/0030267 A1 | 2/2010 | Winslow et al. | |
| 2010/0256760 A1* | 10/2010 | Hansell | 623/17.11 |
| 2011/0276142 A1* | 11/2011 | Niemiec et al. | 623/17.16 |
| 2011/0319998 A1* | 12/2011 | O'Neil et al. | 623/17.16 |
| 2011/0320000 A1* | 12/2011 | O'Neil et al. | 623/17.16 |
| 2012/0130387 A1* | 5/2012 | Simpson et al. | 606/104 |
| 2012/0203345 A1* | 8/2012 | Voorhies | 623/17.16 |
| 2013/0123793 A1* | 5/2013 | Kehres et al. | 606/104 |
| 2013/0150906 A1* | 6/2013 | Kerboul et al. | 606/86 A |
| 2013/0172977 A1* | 7/2013 | Forde et al. | 623/1.11 |
| 2014/0018815 A1* | 1/2014 | Kirschman | 606/99 |
| 2014/0018816 A1* | 1/2014 | Fenn et al. | 606/104 |
| 2014/0058512 A1* | 2/2014 | Petersheim | 623/17.16 |
| 2014/0058513 A1* | 2/2014 | Gahman et al. | 623/17.16 |
| 2014/0172103 A1* | 6/2014 | O'Neil et al. | 623/17.16 |
| 2014/0172105 A1* | 6/2014 | Frasier et al. | 623/17.16 |

* cited by examiner

SYSTEM AND METHOD FOR A LOCKABLE POLYAXIAL DRIVER TOOL

CROSS REFERENCE TO RELATED CO-PENDING APPLICATIONS

This application claims the benefit of U.S. provisional application Ser. No. 61/570,082 filed on Dec. 13, 2011 and entitled SYSTEM AND METHOD FOR A LOCKABLE POLYAXIAL DRIVER TOOL, which is commonly assigned and the contents of which are expressly incorporated herein by reference.

FIELD OF THE INVENTION

The present invention relates to a system and a method for a driver tool for inserting a surgically implantable device, and in particular, to a driver that is lockable and transfers motion to the implantable device through a polyaxial joint.

BACKGROUND OF THE INVENTION

In spine surgical procedures intervertebral spacers, spinal cages or connecting elements, such as rods, plates or wires are implanted and fixed between two adjacent vertebras or two or more other locations of the spine. Placement of these spacers, cages, connecting elements or other implants is desirably performed via minimally invasive spinal surgeries. The orientation of these implants during implantation is critical for the overall success of the procedure. Accordingly there is a need for improved methods, tools and devices that allow insertion of spinal implants in a controlled orientation via minimally invasive surgery.

SUMMARY OF THE INVENTION

The present invention provides a driver tool for inserting a surgically implantable device. The driver is lockable in a precise orientation and transfers motion to the implantable device through a polyaxial joint. In the unlocked position the driver provides polyaxial orientation of the implantable device.

In general, in one aspect, the invention features a polyaxial driver system for inserting and setting the angular orientation of an implant including an elongated component and a distal component. The elongated component extends along a main axis and includes an elongated tubular sheath and an elongated shaft disposed within the tubular sheath. The distal component is pivotally connected to a distal end of the elongated shaft and includes a tubular body extending along the main axis and a spherical head dimensioned to fit and move freely within the tubular body. A proximal end of the elongated shaft includes a first set of outer threads and a proximal end of the elongated tubular sheath includes inner threads shaped and dimensioned to engage the first set of outer threads of the elongated shaft. Rotating the elongated tubular sheath clockwise or counter-clockwise moves the elongated shaft forward or backward along the main axis, respectively.

Implementations of this aspect of the invention may include one or more of the following features. The distal end of the elongated shaft includes a second set of outer threads. The second set of outer threads are shaped and dimensioned to engage inner threads formed in the distal component. Rotating the elongated shaft clockwise or counter-clockwise causes the second set of outer threads to engage or disengage the inner threads of the distal component and thereby the elongated shaft engages or disengages the distal component, respectively. The spherical head is configured to move longitudinally along the main axis and to pivot relative to the main axis within the tubular body. The system further includes a setscrew having a threaded body and a head. The tubular body of the distal component includes a slot extending along the main axis and having a width smaller than the diameter of the setscrew head and larger than the diameter of the setscrew threaded body. The spherical head further includes a threaded opening dimensioned to receive the setscrew. Screwing the setscrew into the spherical head threaded opening secures the position and angular orientation of the spherical head within the tubular body and relative to the main axis. The system further includes a rod extending from the spherical head. The spherical head is oriented within the tubular body of the distal component so that the rod is positioned outside of the tubular body at all times. The rod has outer threads shaped and dimensioned to engage inner threads formed within an opening of an implant. The rod has a bayonet connector and is configure to connect to an implant via the bayonet connector. The system further includes a handle configured to be attached to the proximal end of the elongated shaft. The handle has a cylindrical body having a thumb indentation configured to provide tactile control of the orientation of an implant attached to the distal component. A distal end of the tubular sheath includes the tubular body of the distal component.

In general, in one aspect, the invention features a method for inserting and setting the angular orientation of an implant including the following. First, providing an elongated component extending along a main axis and comprising an elongated tubular sheath and an elongated shaft disposed within the tubular sheath. Next, providing a distal component and pivotally connecting the distal component to a distal end of the elongated shaft. The distal component includes a tubular body extending along the main axis and a spherical head dimensioned to fit and move freely within the tubular body. A proximal end of the elongated shaft includes a first set of outer threads and a proximal end of the elongated tubular sheath includes inner threads shaped and dimensioned to engage the first set of outer threads of the elongated shaft. Rotating the elongated tubular sheath clockwise or counter-clockwise moves the elongated shaft forward or backward along the main axis, respectively. The spherical head includes a threaded opening dimensioned to receive a setscrew. Screwing the setscrew into the spherical head threaded opening secures the position and angular orientation of the spherical head within the tubular body and relative to the main axis. The method further includes attaching an implant to the distal component, setting and locking the position and angular orientation of the distal component relative to the main axis, rotating the elongated tubular sheath clockwise to move the elongated shaft forward along the main axis over the setscrew and inserting the implant.

Among the advantages of this invention may be one or more of the following. The lockable polyaxial driver tool of this invention provides flexibility and accuracy in the positioning and orientation of an implant. The precise orientation of the implant may reduce the duration of the surgical procedure and may contribute to the overall therapeutic success of the surgery.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

The present invention provides a driver tool for inserting a surgically implantable device. The driver tool includes a handle and an elongated shaft with a polyaxially attachable distal end. The orientation of the distal end is lockable and transfers motion to the implantable device through a polyaxial joint. In the unlocked position the driver provides at least three degrees of freedom motion to the implantable device.

Figure 1:
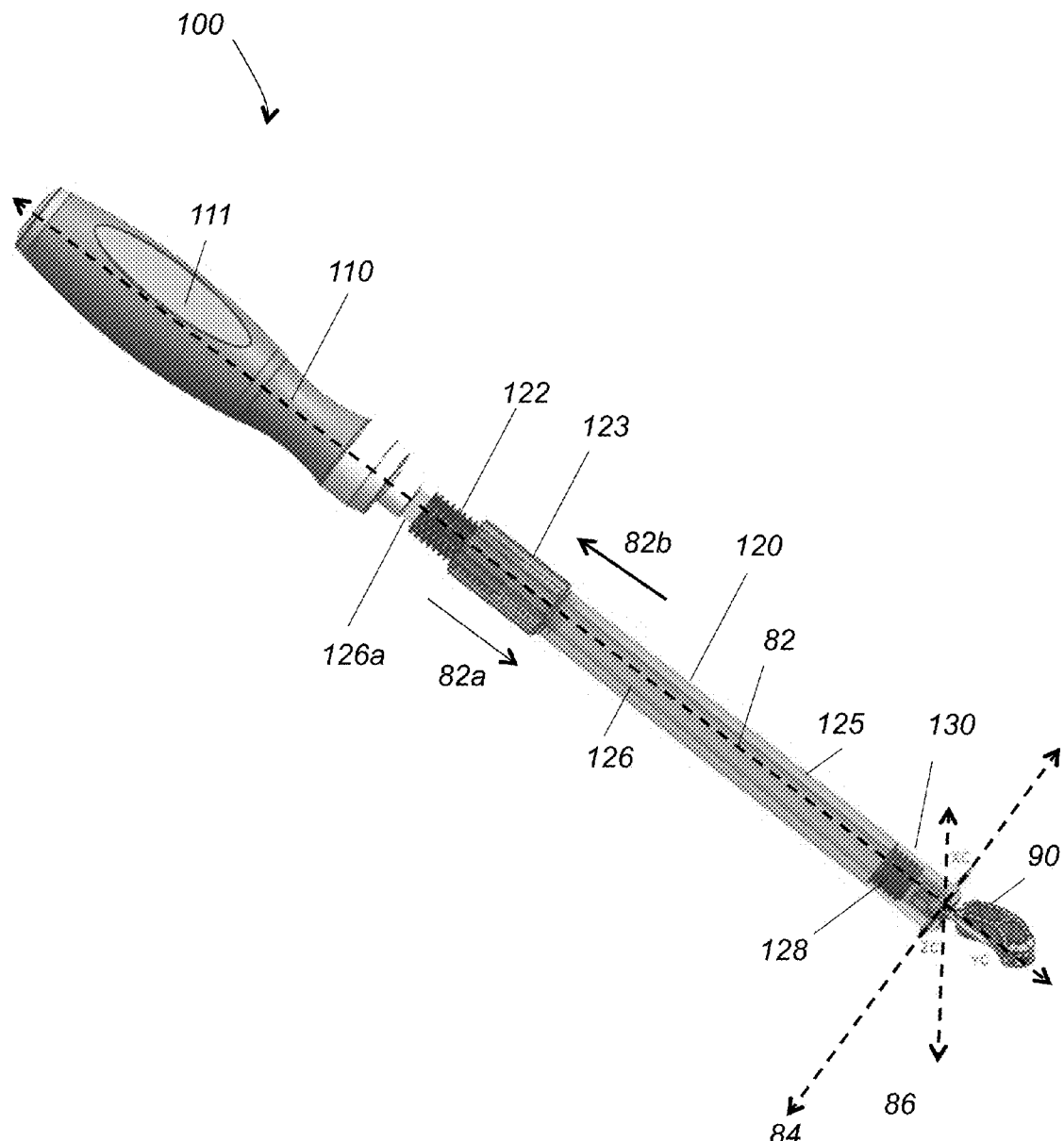
FIG. 1 is a perspective view of a lockable polyaxial driver of this invention.
Figure 6:
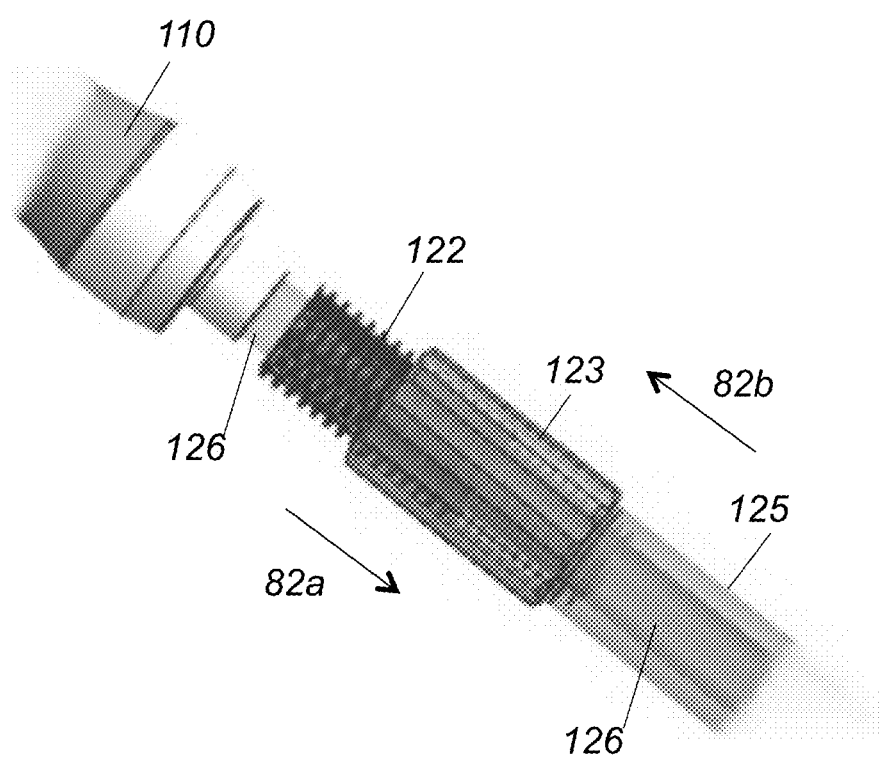
FIG. 6 is an enlarged perspective view of the handle connection to the lockable polyaxial driver of FIG. 1.

Referring to FIG. 1, driver tool 100 includes an elongated component 120, a handle 110 and a distal component 130. The elongated component 120 extends along axis 82 and includes an elongated tubular outer sheath 125 and an elongated shaft 126 disposed within the outer sheath 125. The proximal end 126a of the elongated shaft 126 is attached to the handle 110 and includes a first set of outer threads 122. Outer threads 122 are shaped and dimensioned to engage inner threads 123 formed in the inner surface of the proximal end of outer sheath 125. Rotating the outer sheath 125 clockwise or counter-clockwise threads the first set of outer threads 122 into or out of the outer sheath 125 and moves the elongated shaft 126 forward or backward along the directions 82a or 82b, respectively, as shown in FIG. 1 and FIG. 6.

Figure 2:
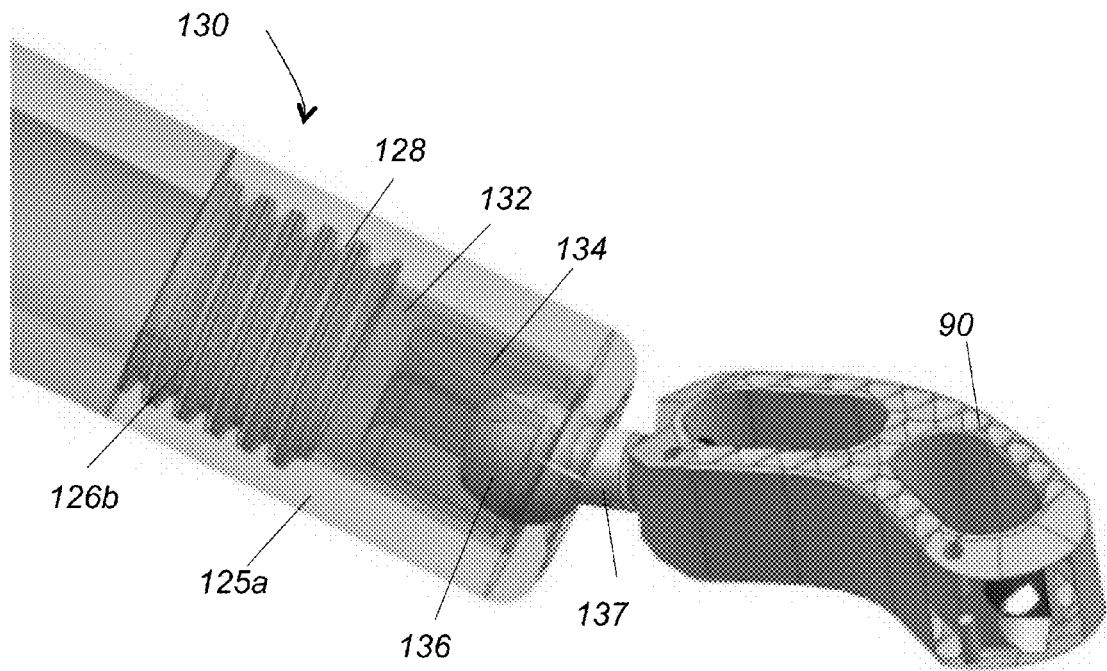
FIG. 2 is an enlarged perspective view of the distal end of the lockable polyaxial driver of FIG. 1.
Figure 3:
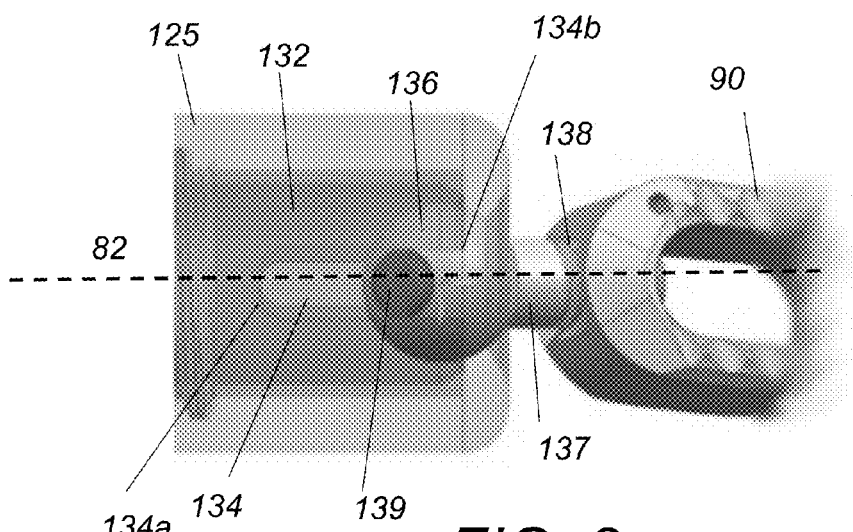
FIG. 3 is a top perspective view of the distal end of the lockable polyaxial driver of FIG. 1.
Figure 4:
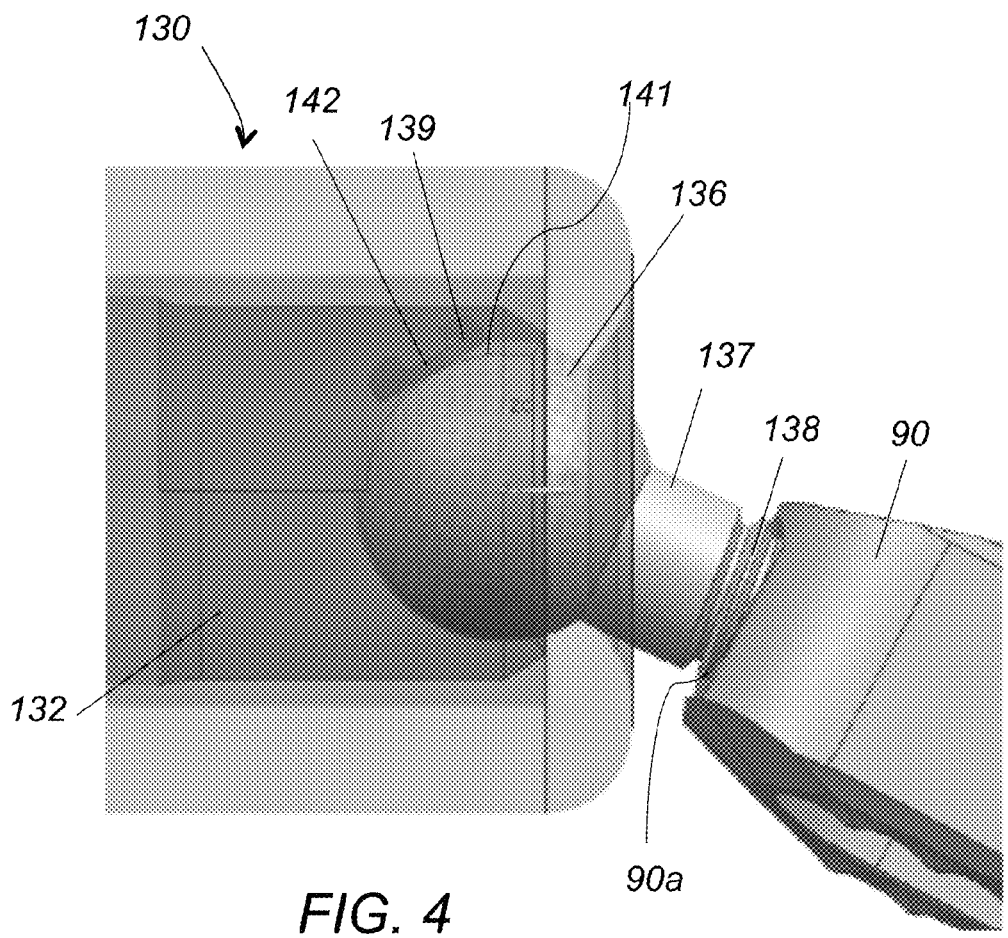
FIG. 4 is a side view of the distal end of the lockable polyaxial driver of FIG. 1.
Figure 5:
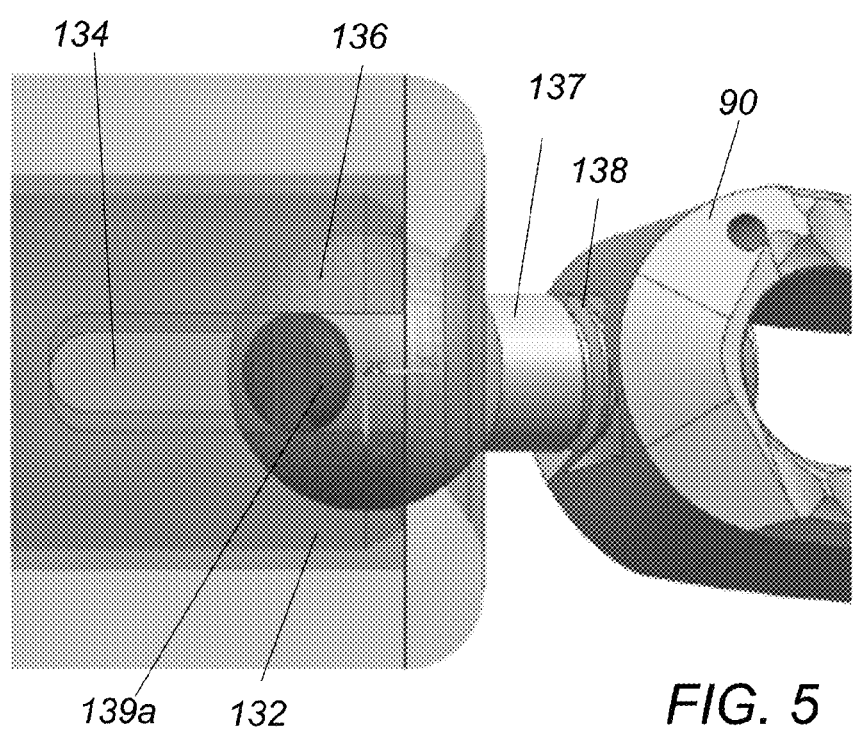
FIG. 5 is an enlarged top view of the distal end of the lockable polyaxial driver of FIG. 1.

Referring to FIG. 2, the distal end 126b of the elongated shaft 126 includes a second set of outer threads 128. Outer threads 128 are shaped and dimensioned to engage inner threads formed in the distal component 130. Rotating the handle 110 clockwise or counter-clockwise threads the outer threads 128 into or out of the distal component 130 and thereby engages or disengages the distal component 130, respectively. Distal component 130 includes a cylindrically shaped tubular body 132 having a slot 134. Slot 134 is formed on the side surface of body 132, extends along the elongated axis 82 and has a closed end 134a and an open-end 134b. Distal component 130 also includes a spherical head 136 dimensioned to fit and move freely within the tubular body 132. Spherical head 136 moves longitudinally along axis 82, and rotates around axis 82. Spherical head 136 is also dimensioned to pivot relative to axis 82 and to assume any angle relative to the plane formed by the two intersecting axes 84 and 86 that are perpendicular to axis 82 and perpendicular to each other, as shown in FIG. 1. Spherical head 136 also includes a rod 137 extending from its base and the head 136 is oriented within the tubular body 132, so that rod 137 is positioned outside of the tubular body 132 at all times. Rod 137 includes outer threads 138 at its distal end and the outer threads 138 are shaped and dimensioned to engage inner threads formed in a cavity or a through aperture 90a of the implant 90, as shown in FIG. 4. Threading outer threads 138 into or out of threaded aperture 90a attaches or detaches implant 90 to or from the driver tool 100, respectively. The top of spherical head 136 also includes a threaded opening 141 dimensioned to receive a setscrew 139. Setscrew 139 includes a threaded body (not shown) and a head 139a. Setscrew head 139a has a diameter that is slightly larger than the width of the elongated slot 134 and the threaded body has a diameter that is slightly smaller than the width of the elongated slot 134. The dimensions of the set screw 139 are chosen so that the threaded body is placed through the elongated slot 134 and is threaded into the threaded opening 141 of the spherical head 136 and the setscrew head 139a remains above the elongated slot 134, thereby securing the orientation of the spherical head 136 within the tubular body 132. The setscrew head 139a includes a slot 142 used for engaging a screwdriver. Handle 110 includes a cylindrical body having a thumb indentation 111 used to provide tactile control of the implant 90 orientation.

In operation, implant 90 is attached to the distal component 130 by threading threads 138 into the aperture 90a and then its orientation is set relative to the plane defined by the intersecting axes 84, 86 at any desired angle by pivoting and rotating the spherical head 136 within the tubular body 132. Once the implant's desired orientation is set, the set screw 139 is placed through the elongated slot 134 and is screwed into the spherical head opening 141 to secure the spherical head 136 within the tubular body 132 and to prevent it from any further movement. Next, the outer sheath 125 is rotated clockwise to move its position along direction 82a until its distal end 125a is placed over the tubular body 132. In this configuration, the distal end 125a of the tubular sheath 125 covers the access to the setscrew 139 and provides a smooth outer surface. The implant 90 then is implanted in the desired location and then the handle 110 is rotated counterclockwise to disengage the rod 137 from the implant 90. The lockable polyaxial driver tool 100 is used to implant a spinal cage, or any other intervertebral implant, or any other implant that requires precise orientation.

Other embodiments include one or more of the following. Distal component 130 and the tubular outer sheath 125 form a single component. Rod 138 may be attached to the spherical head 136 via a bayonet fitting.

Several embodiments of the present invention have been described. Nevertheless, it will be understood that various modifications may be made without departing from the spirit and scope of the invention. Accordingly, other embodiments are within the scope of the following claims.

What is claimed is:

1. A polyaxial driver system for inserting and setting the angular orientation of an implant comprising:

an elongated component extending along a main axis and comprising an elongated tubular sheath and an elongated shaft disposed within the tubular sheath;

a distal component configured to be pivotally connected to a distal end of the elongated shaft and comprising a tubular body extending along said main axis and a spherical head dimensioned to fit and move freely within the tubular body; and wherein a proximal end of the elongated shaft comprises a first set of outer threads and a proximal end of the elongated tubular sheath comprises inner threads shaped and dimensioned to engage the first set of outer threads of the elongated shaft and wherein rotating the elongated tubular sheath clockwise or counter-clockwise moves the elongated shaft forward or backward along the main axis, respectively;

wherein the distal end of the elongated shaft comprises a second set of outer threads and wherein said second set of outer threads are shaped and dimensioned to engage inner threads formed in the distal component and wherein rotating the elongated shaft clockwise or counter-clockwise causes said second set of outer threads to engage or disengage the inner threads of the distal component and thereby the elongated shaft engages or disengages the distal component, respectively;

wherein the spherical head is configured to move longitudinally along the main axis and to pivot relative to the main axis within the tubular body; and wherein the system further comprises a setscrew having a threaded body and head and wherein the tubular body of the distal component comprises a slot extending along the main axis and having a width smaller the diameter of the setscrew head and larger than the diameter of the setscrew threaded body.

2. The system of claim 1, wherein the spherical head further comprises a threaded opening dimensioned to receive the setscrew and wherein screwing the setscrew into the spherical head threaded opening secures the position and angular orientation of the spherical head within the tubular body and relative to the main axis.

3. The system of claim 1, further comprising a rod extending from the spherical head and wherein the spherical head is oriented within the tubular body of the distal component so that the rod is positioned outside of the tubular body at all times.

4. The system of claim 3, wherein said rod comprises outer threads shaped and dimensioned to engage inner threads formed within an opening of an implant.

5. The system of claim 3, wherein said rod comprises a bayonet connector and is configure to connect to an implant via the bayonet connector.

6. The system of claim 5, wherein said handle comprises a cylindrical body having a thumb indentation configured to provide tactile control of the orientation of an implant attached to the distal component.

7. The system of claim 1, further comprising a handle configured to be attached to the proximal end of the elongated shaft.

8. The system of claim 1, wherein a distal end of the tubular sheath comprises the tubular body of the distal component.

9. A method for inserting and setting the angular orientation of an implant comprising:

providing an elongated component extending along a main axis and comprising an elongated tubular sheath and an elongated shaft disposed within the tubular sheath;

providing a distal component and pivotally connecting the distal component to a distal end of the elongated shaft;

wherein the distal component comprises a tubular body extending along said main axis and a spherical head dimensioned to fit and move freely within the tubular body; and wherein a proximal end of the elongated shaft comprises a first set of outer threads and a proximal end of the elongated tubular sheath comprises inner threads shaped and dimensioned to engage the first set of outer threads of the elongated shaft and wherein rotating the elongated tubular sheath clockwise or counter-clockwise moves the elongated shaft forward or backward along the main axis, respectively;

wherein the distal end of the elongated shaft comprises a second set of outer threads and wherein said second set of outer threads are shaped and dimensioned to engage inner threads formed in the distal component and wherein rotating the elongated shaft clockwise or counter-clockwise causes said second set of outer threads to engage or disengage the inner threads of the distal component and thereby the elongated shaft engages or disengages the distal component, respectively;

wherein the spherical head is configured to move longitudinally along the main axis and to pivot relative to the main axis within the tubular body; and providing a setscrew having a threaded body and head and wherein the tubular body of the distal component comprises a slot extending along the main axis and having a width smaller the diameter of the setscrew head and larger than the diameter of the setscrew threaded body.

10. The method of claim 9, wherein the spherical head further comprises a threaded opening dimensioned to receive the setscrew and wherein screwing the setscrew into the spherical head threaded opening secures the position and angular orientation of the spherical head within the tubular body and relative to the main axis.

11. The method of claim 10 further comprising:

attaching an implant to the distal component;

setting and locking the position and angular orientation of the distal component relative to the main axis;

rotating the elongated tubular sheath clockwise to move the elongated shaft forward along the main axis over the setscrew; and inserting the implant.

12. The method of claim 9, further comprising providing a rod extending from the spherical head and wherein the spherical head is oriented within the tubular body of the distal component so that the rod is positioned outside of the tubular body at all times.

13. The method of claim 12, wherein said rod comprises outer threads shaped and dimensioned to engage inner threads formed within an opening of an implant.

14. The method of claim 12, wherein said rod comprises a bayonet connector and is configure to connect to an implant via the bayonet connector.

15. The method of claim 9, further comprising providing a handle configured to be attached to the proximal end of the elongated shaft.

16. The method of claim 15, wherein said handle comprises a cylindrical body having a thumb indentation configured to provide tactile control of the orientation of an implant attached to the distal component.

17. The method of claim 9, wherein a distal end of the tubular sheath comprises the tubular body of the distal component.

* * * * *